United States Patent
Dominguez De Matos et al.

(10) Patent No.: US 10,221,375 B2
(45) Date of Patent: Mar. 5, 2019

(54) GLYCEROL ESTER PRODUCTION FROM WASTES CONTAINING ORGANIC OILS AND/OR FATS

(71) Applicant: RESIWAY—SOLUCOES SUSTENTAVEIS, LDA., Canelas-Vila Nova de Gaia (PT)

(72) Inventors: Ana Luisa Dominguez De Matos, Espinho (PT); Albina Raquel Morais Sequeira, Viana do Castelo (PT)

(73) Assignee: RESIWAY—SOLUCOES SUSTENTAEIS, LDA., Canelas-Vila Nova de Gaia (PT)

( * ) Notice: Subject to any disclaimer, the term of this patent is extended or adjusted under 35 U.S.C. 154(b) by 0 days.

(21) Appl. No.: 15/757,572

(22) PCT Filed: Sep. 12, 2016

(86) PCT No.: PCT/IB2016/055422
§ 371 (c)(1),
(2) Date: Mar. 5, 2018

(87) PCT Pub. No.: WO2017/042750
PCT Pub. Date: Mar. 16, 2017

(65) Prior Publication Data
US 2019/0040337 A1    Feb. 7, 2019

(30) Foreign Application Priority Data
Sep. 11, 2015 (PT) .......... 108810

(51) Int. Cl.
*C11C 3/02* (2006.01)
*C11B 3/00* (2006.01)
(Continued)

(52) U.S. Cl.
CPC ............ *C11C 3/02* (2013.01); *B01D 17/0217* (2013.01); *B01D 21/0012* (2013.01);
(Continued)

(58) Field of Classification Search
CPC ........... C11C 3/02; C07C 67/03; C07C 67/08; C11B 3/008; B01D 17/0217; B01D 21/0012; B01D 21/262
See application file for complete search history.

(56) References Cited

U.S. PATENT DOCUMENTS

| | | | |
|---|---|---|---|
| 6,500,974 B2 * | 12/2002 | Thengumpillil | C07C 67/08 554/161 |
| 2010/0059450 A1 * | 3/2010 | Lafosse | C11B 3/04 210/708 |
| 2014/0221675 A1 * | 8/2014 | Agarwal | C11B 3/14 554/173 |

FOREIGN PATENT DOCUMENTS

| | | |
|---|---|---|
| EP | 2272818 A1 | 1/2011 |
| GB | 183897 A | 8/1922 |
| WO | 2013156953 A1 | 10/2013 |

OTHER PUBLICATIONS

International Search Report and Written Opinion dated Jan. 19, 2017 for PCT/IB2016/055422.

* cited by examiner

*Primary Examiner* — Yate' K Cutliff
(74) *Attorney, Agent, or Firm* — Lucas & Mercanti, LLP

(57) ABSTRACT

The present invention describes a two stage process comprising a first stage of extraction of oils and/or fats with free fatty acids (FFA) from wastes originated in waste water treatment plants (WWTP), generally known as brown grease, grease traps, from WWTP of several food and dairy industries and from processing animal products, or other waste streams containing organic oils and/or fats and a
(Continued)

second stage of conversion of the FFA obtained in the first stage into glycerol ester by a glycerolysis reaction without the presence of a catalyst.

8 Claims, 1 Drawing Sheet

(51) Int. Cl.
  *B01D 17/02* (2006.01)
  *B01D 21/26* (2006.01)
  *B01D 21/00* (2006.01)
  *C07C 67/08* (2006.01)
(52) U.S. Cl.
  CPC ............ *B01D 21/262* (2013.01); *C11B 3/008* (2013.01); *C07C 67/08* (2013.01)

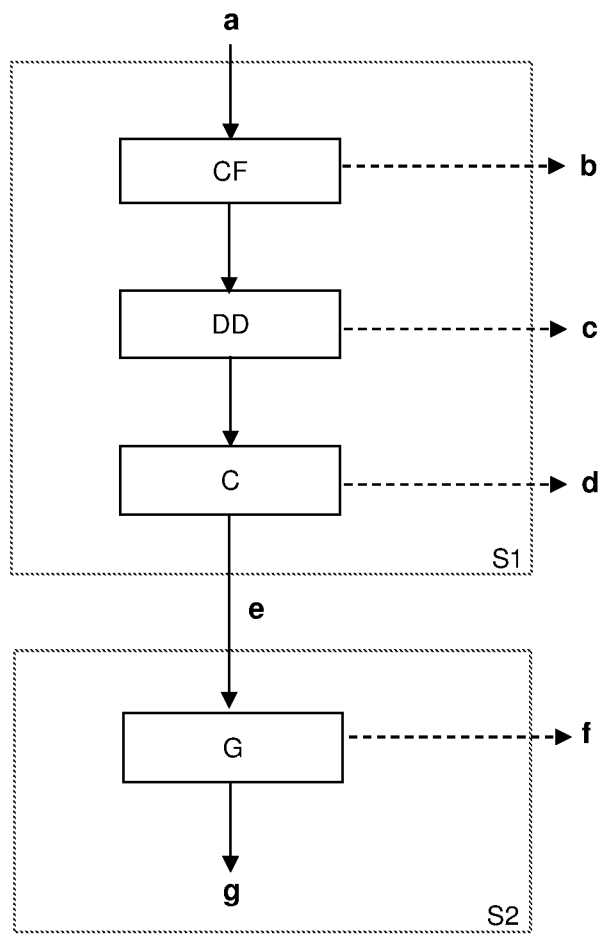

GLYCEROL ESTER PRODUCTION FROM WASTES CONTAINING ORGANIC OILS AND/OR FATS

CROSS REFERENCE TO RELATED APPLICATION

This Application is a 371 of PCT/IB2016/055422 filed on Sep. 12, 2016 which, in turn, claimed the priority of Portuguese Patent Application No. 108810 filed on Sep. 11, 2015, both applications are incorporated herein by reference.

TECHNICAL FIELD

The present application describes a process to recover FFA from waste streams with organic oils and/or fats, aiming its transformation in a glycerol ester.

BACKGROUND

Increasing demand in energy requirement, associated with EU regulations, are compelling the attention on alternate fuels. The change from a fossil fuel to a biofuel is being highly associated with the waste management technologies, with significant environmental and economic benefits, by valorising specific waste streams. Certain types of wastes might present significant organic oil and fat contents, such as those originated in waste water treatment plants (WWTP), generally known as brown grease, grease traps, from WWTP of several food and dairy industries and from processing animal products. Such wastes are difficult to treat, namely due to its heterogeneous composition, presenting high levels of solids, water and free fatty acids (FFA) and usually end up being landfilled, although waste management policies discourages such conduction, or directed to composting plants.

In addition, oils and fats with high FFA content are not suitable to be used directly in the conventional biofuel production process. FFA is undesirable during the alkali transesterification process due to the formation of soap, yield loss, and increased difficulty in product separation. Waste streams of organic oils and fats that are recovered from waste water treatment plants (WWTP), generally known as brown grease, grease traps and from WWTP of several food and dairy industries can contain considerable amounts of FFA. Depending on the source of the raw material, FFA content may be between 0% (w/w) and 100% (w/w), nevertheless the referred waste streams of organic oils and fats from waste water treatment plants (WWTP), generally known as brown grease, grease traps and from WWTP of several food and dairy industries generally have FFA content higher than 50% (w/w).

The present invention disclosures a process to extract and valorise FFA from waste streams containing potentially high content of organic oils and/or fats, such as brown grease, oils/fats from grease traps or from WWTP of food industries, which, because of their high content of FFA, would otherwise not be valorised, being mainly landfilled, with the associated negative environmental impact. This new process of waste treatment is a two stage process, where the first stage consists in a physical treatment to extract and recover the oils and/or fats from the waste stream, and the second stage is a glycerolysis reaction where the FFA present in the oils and/or fats, recovered in the first stage, is transformed in a glycerol ester.

EP 1051386B1 discloses a process for the production of monoglycerides by glycerolysis of methyl ester derived from animal or vegetable fat and oils.

EP0334154 discloses FFA esterification with sulphuric acid, toluene sulphonic acid, cholorosulfonic acid and methylsulphonic acids in alcohol, while U.S. Pat. No. 6,965,044 discloses the esterification of acid oils or fats with sulphuric acid along with methanol.

Further methods for esterification of FFA using different type of solid catalyst are described, such as ion exchange resins (EP20070254389, EP1921131 and U.S. Pat. No. 7,256,301). US2011/0105775A1 discloses the use of an acidic solid catalyst dissolved in an alcohol.

SUMMARY

The present application discloses a process for the production of glycerol ester from a waste stream containing between 25% (w/w) and 50% (w/w) of organic oil and/or fat, with free fatty acids (FFA), comprising the following steps:
  coarse filtration, where process water at 80° C. is used to liquefy the oil and/or fat content in the waste stream to enhance the dynamic decantation step, wherein solids of size higher than 15 mm are separated and removed;
  dynamic decantation step wherein solids of size higher than 1 mm are separated and removed;
  centrifugation step at a temperature between 80° C. to 90° C. wherein a resulting acidic oil stream has a water content inferior to 5% (w/w) and a content of FFA, higher than 50% (w/w);
  glycerolysis reaction step of the acidic oil stream, obtained in the previous step, with glycerol and without the use of a catalyst.

In an embodiment, the filtered waste stream from the coarse filtration step is maintained at a temperature between 40° C. and 85° C. and with maximum agitation of 20 rpm.

In another embodiment, in the dynamic filtration step, the differential speed varies between 5 rpm and 15 rpm and the liquid output radius level varies between 102 mm and 106 mm.

In yet another embodiment, in the centrifugation step, the centrifugation time varies between 15 min and 99 min and liquid output radius level is between 102 mm and 127 mm.

In another embodiment, in the glycerolysis reaction step, the glycerol is added during the reaction time.

In yet another embodiment, the glycerolysis reaction temperature is at 200° C.

In another embodiment, in the glycerolysis reaction step, the pressure varies from 1000 mbar to 50 mbar.

In yet another embodiment, after the glycerolysis step, the non-reacted glycerol is separate from the glycerol ester stream by decantation.

BRIEF DESCRIPTION OF DRAWINGS

Without intent to limit the disclosure herein, this application presents attached drawings of illustrated embodiments for an easier understanding.

FIG. 1: Schematic representation of glycerol ester production from wastes containing organic oils and/or fats, which has been used in an embodiment of the process described in the present disclosure, where: S1 represents the first stage of the process and S2 represents the second stage of the process; a represents the waste stream of organic oils and/or fats from waste water treatment plants (WWTP), generally known as brown grease, grease traps and from WWTP of several food and dairy industries, or other waste streams containing organic oils and/or fats; b represents the filtrate obtained from the coarse filtration step (CF) containing solids which size is higher than 15 mm; c represents the stream containing solids which size is higher than 1 mm and water obtained from the dynamic decantation step (DD); d represents the stream containing residual solids which size is lower than 1 mm and water obtained from the high speed centrifugation step (C); e represents the stream resulting from the high speed centrifugation step containing oil and/or fat stream with a high content of FFA, also designated an acidic oil stream; f represents the stream resulting from the glycerolysis step (G) containing water and non-reacted glycerol; and g represents the stream resulting from the glycerolysis step containing glycerol ester.

DESCRIPTION OF THE EMBODIMENTS

Referring to the drawings, herein are described optional embodiments in more detail, which however are not intended to limit the scope of the present application.

The present invention relates to a process to extract and valorise oil and/or fats, whit high content on FFA, from waste streams containing organic oils and/or fats, in a first stage, and a second stage in a glycerolysis reaction where the FFA is transformed in a glycerol ester. The first stage consist on a physical extraction and the second stage consist on a chemical transformation.

The waste streams to be processed are those with significant content of organic oils and/or fats, between 25% (w/w) and 50% (w/w), such as waste streams of organic oils and fats from waste water treatment plants (WWTP), generally known as brown grease, oils/fats from grease traps or from WWTP of food and dairy industries.

Due to the heterogeneity and composition of this waste, namely high content of solids and water, physical methods are applied in order to extract the oil and/or fat content of the stream. Solid content can be removed by conventional methods such as by coarse filtration (solids higher than 15 mm) proceeded by dynamic decantation for reduce its content to values less than 1% (w/w).

Due to the different liquid phase densities, water can be removed by high speed centrifugation obtaining in the end an oil and/or fat stream, also designated an acidic oil stream with a water content inferior to 5% (w/w) and a considerable high content of FFA.

In a second stage of the process, this acidic oil with high FFA content is then treated by a glycerolysis reaction, in order to transform the FFA in mono-, di- and triglycerides.

In the first stage of this invention the selected waste stream is submitted, to a three steps physical treatment, without any chemical addition, to extract and recover oil and/or fat, with a considerable high content of FFA, from the waste streams. The physical method consists, in a first step, on the solids removal from the raw stream by coarse filtration, where solids with a size higher than 15 mm are removed.

In the coarse filtration step, process water at 80° C. is used to liquefy the oil and/or fat content in the waste stream to enhance the dynamic decantation step and to remove solids with size higher than 15 mm. This filtered waste stream is then storage in heated and agitated tanks were the temperature is maintained between 40° C. and 85° C. and with maximum agitation of 20 rpm to avoid fat emulsification.

In the dynamic decantation step, the differential speed and the liquid output radius level will be adjusted according to the type of waste, solid content and the kind of solids present in the waste stream, namely settleable solids and suspended solids but not limited to the same, and oil and fats content. The differential speed varies between 5 rpm and 15 rpm and the liquid output radius level between 102 mm and 106 mm. In the end of this filtration step, a stream containing oil and/or fats, water and solid content<1% (w/w) is obtained.

On the third step, the water and also some remaining solids are removed by high speed centrifugation (nearly 5200 rpm). The centrifugation step occurs in a temperature range of 80° C. to 90° C., centrifugation time between 15 min and 99 min and liquid output radius level between 102 mm and 127 mm. The centrifugation time adjustment will be determinant to avoid solid accumulation in the operation. In the end an oil stream with a water content inferior to 5% (w/w) and a considerable high content of FFA, higher than 50%, is obtained.

The FFA recovery yield of this first stage is between 65% (w/w) to 85% (w/w).

The operation parameters have to be adjusted according to the characteristics of the input material that due to its origin—waste stream—is very heterogeneous in terms of solid, water and oil content. The process temperature is between the room temperature and 90° C. and at atmospheric pressure. Room temperature is considered to be a temperature, in which the person is accustomed to work comfortably, ranging approximately between 15° C. to 30° C., preferably from 20° C. to 25° C., more preferably between 21° C. and 23° C., however without restricting temperatures above or below these limits and provided acceptable and recognized as ambient temperature or "room temperature", i.e. the building interior. The first stage process, comprising the referred three physical treatment steps, can be a continuous or batch process.

The second stage of the process consists in the chemical conversion of the FFA present in the oil stream by glycerolysis reaction in the absence of a catalyst, by which the FFA react with glycerol being converted into glycerol ester, namely mono-, di- and triglycerides and water. The reaction can be summarized as follows:

$$R\text{-}COOH + C_3H_5(OH)_3 \leftrightarrow H_2O + R\text{-}CO\text{—}OH_2C\text{—}C_3H_5 \qquad (1)$$

wherein R are hydrocarbon chains.

The operation of this second stage is a batch process. The oil and/or fat, with high content of FFA (higher than 50%), obtained on the first stage, or from some other oil and/or fat stream, with high content of FFA (higher than 50%), enters in to the reactor (filing step), where; on this filing step the glycerol is also added during the course of the reaction, according to the content of mono-, di- and triglycerides desired.

The chemical reaction is highly endothermic being conducted at high temperature and low pressure, therefore the content of the reactor is heated during the filling procedure until the temperature reaches 200° C. If after the filling step the required temperature is not achieved, heating continues till the 200° C. This temperature is maintained during the glycerolysis reaction.

The glycerolysis reaction is also dependent upon the glycerol used. The amount of glycerol needed for the glycerolysis reaction is determined attending to the estequiometric relation and according to FFA level on the raw feed stream (FIG. 1, a) and the FFA residual level desired on the glycerol ester stream (FIG. 1, g) to be produced. The moment of adding the glycerol is determined according to the content of mono-, di- and triglycerides desired. If all the glycerol is added on the beginning, on the filling step along with the FFA, it is promoted the production of monoglycerides, which is the simplest glycerolysis reaction. If glycerol addition is dosed along the reaction it is promoted the production of di and tri glycerides.

During the reaction the mixture is agitated, the temperature is maintained at 200° C. and the pressure controlled. The water content and acidity on the mixture is verified hourly.

The chemical reaction is reversible so, in order to shift the reaction towards the products, water is removed from the reaction as it is being generated. The water removal, along with other vapours, is achieved by reducing the pressure. The reaction pressure variates between the atmospheric level and 50 mbar. In the beginning of the reaction the pressure is nearly 1000 mbar, as the vapours are being produce the pressure is reduce and it can achieve 50 mbar. The pressure control must ensure that glycerol vaporization is minimum, to guarantee efficiency on the consumable use. The vapours are then removed to a condensate vessel. The reaction time depends on the FFA levels in the feed, the levels required on the output and on water content desired. For an 8 $m^3$ batch with FFA>80% (w/w) and water<5% (w/w), the average duration of the reaction is 6 hours to achieve FFA<1% (w/w) and water<500 ppm.

The reaction is stopped when the desired content of FFA and water are achieved. The minimum outputs that can be achieved are FFA<1% (w/w) and water<500 ppm. In the end, the oil with low FFA content produced is transferred to a settling tank were the non-reacted glycerol is separated by decantation from the oil, due to their densities difference, for future reutilization.

An additional advantage of using the described two-stage process is that the glycerolysis reaction of the second stage can be performed in the absence of catalyst and therefore not requiring additional purification operations of the end product which lead to product loss and a lower overall yield of the process. The fact that no further operations are necessary also reduces the complexity of the overall described process.

WORKING EXAMPLE

These working examples illustrate the disclosure but do not intend to imply restrictively any limitations on the scope of the present disclosure.

The process consist on the extraction of acidic oil/FFA from a waste stream by decantation and centrifugation and the glycerolysis reaction of the acidic oil/FFA with glycerol. For the glycerolysis reaction, the experimental set-up included a reaction vessel of stainless steel with 250 mL, a condenser connected to a vacuum pump and a mechanical agitator with adjustable revolution control. The temperature in the reaction vessel was controlled by electrical heating.

Dry matter (consisting of solids, oil and fat), humidity and oils and fats were determined in the waste stream and acidity was determined both in acidic oil and in the glycerol ester.

All experiments described hereafter were carried out in batch and always using the same equipment.

Example 1

| Stage 1 | Waste origin | WWTP |
|---|---|---|
| Acidic oil/ FFA extraction | Waste mixture temperature | 80° C. |
| | Decantation time | 4 h |
| | Centrifugation speed | 4000 rpm |
| | Centrifugation time | 20 min |

-continued

| Stage 2 | Reaction mixture | 50 g acidic oil/FFA |
|---|---|---|
| Acidic oil/ FFA glycerolysis | Reaction conditions | 25 g glycerol<br>Temperature 20° C.<br>Agitation 100 rpm<br>Time 2.5 h |

| Experimental results |
|---|

| Waste stream characterization | |
|---|---|
| Dry matter | 44.5% (w/w) |
| Humidity | 55.6% (w/w) |
| Oils and fats | 12.7% (w/w) |
| Acidic oil/FFA characterization | |
| Acidity | 57.8% (w/w) |
| Glycerol ester characterization | |
| Acidity | 2.43% (w/w) |

Example 2

| Stage 1 | Waste origin | Grease traps |
|---|---|---|
| Acidic oil/ FFA extraction | Waste mixture temperature | 80° C. |
| | Decantation time | 12 h |
| | Centrifugation speed | 4000 rpm |
| | Centrifugation time | 30 min |
| Stage 2 | Reaction mixture | 50 g acidic oil/FFA |
| Acidic oil/ FFA glycerolysis | Reaction conditions | 25 g glycerol<br>Temperature 200° C.<br>Agitation 100 rpm<br>Time 7 h |

| Experimental results |
|---|

| Waste stream characterization | |
|---|---|
| Dry matter | 65.7% (w/w) |
| Humidity | 34.3% (w/w) |
| Oils and fats | 27.8% (w/w) |
| Acidic oil/FFA characterization | |
| Acidity | 73.3% (w/w) |
| Glycerol ester characterization | |
| Acidity | 1.2% (w/w) |

Naturally, the present embodiments are not in any way limited to the embodiments described in this document and a person with average knowledge in the field will be able to predict many possible changes to it without deviating from the main idea, as described in the claims.

The invention claimed is:

1. A process for the production of glycerol ester from a waste stream containing between 25% (w/w) and 50% (w/w) of organic oil and/or fat, with free fatty acids (FFA), comprising the following steps:
   coarse filtration by processing water at 80° C. to liquefy the oil and/or fat content in the waste stream to enhance the dynamic decantation step, wherein solids of size higher than 15 mm are separated and removed;
   dynamic decantation by separating and removing solids of size higher than 1 mm;
   centrifugating at a temperature between 80° C. to 90° C. wherein a resulting acidic oil stream has a water content inferior to 5% (w/w) and a content of FFA, higher than 50% (w/w);

undergoing a glycerolysis reaction step of the acidic oil stream, obtained in the previous step, with glycerol and without the use of a catalyst.

2. The process according to claim 1, wherein a filtered waste stream from the coarse filtration step is maintained at a temperature between 40° C. and 85° C. and with maximum agitation of 20 rpm.

3. The process according to claim 1, wherein in the dynamic filtration step, the differential speed varies between 5 rpm and 15 rpm and the liquid output radius level varies between 102 mm and 106 mm.

4. The process according to claim 1, wherein in the centrifugation step, the centrifugation time varies between 15 min and 99 min and liquid output radius level is between 102 mm and 127 mm.

5. The process according to claim 1, wherein in the glycerolysis reaction step, the glycerol is added during the reaction time.

6. The process according to claim 1, wherein in the glycerolysis reaction temperature is at 200° C.

7. The process according to claim 1, wherein in the glycerolysis reaction step, the pressure varies from 1000 mbar to 50 mbar.

8. The process according to claim 1, wherein after the glycerolysis step, the non-reacted glycerol is separate from the glycerol ester stream by decantation.

\* \* \* \* \*